US006620624B1

(12) United States Patent

Nishi

(10) Patent No.: US 6,620,624 B1

(45) Date of Patent: Sep. 16, 2003

(54) MASS SPECTROMETRY INTERFACE, A MASS SPECTROMETER AND A MASS SPECTROMETRY

(75) Inventor: Nobuyuki Nishi, Aichi Pref. (JP)

(73) Assignee: Okazaki National Research Institutes, Aichi Pref. (JP)

( * ) Notice: Subject to any disclaimer, the term of this patent is extended or adjusted under 35 U.S.C. 154(b) by 140 days.

(21) Appl. No.: 09/684,441

(22) Filed: Oct. 6, 2000

(30) Foreign Application Priority Data

Aug. 10, 2000 (JP) ....................................... 2000-242002

(51) Int. Cl.[7] ................................................ G01N 33/00

(52) U.S. Cl. ........................ 436/173; 250/281; 250/282; 250/288; 436/85; 436/86; 436/87; 436/88; 436/89; 436/90; 436/91; 436/92; 436/93; 436/94; 436/95; 436/96

(58) Field of Search ............................. 436/85–96, 173; 250/281–282, 287–288

(56) References Cited

U.S. PATENT DOCUMENTS 4,740,298 A * 4/1988 Andresen et al. ......... 210/198.2
6,175,112 B1 * 1/2001 Karger et al. ............... 250/288

FOREIGN PATENT DOCUMENTS

JP 60-146438 8/1985
JP 9-326243 12/1997
JP 2002-502543 1/2002
WO 98/53308 * 11/1998

OTHER PUBLICATIONS

E. D. Hardin et al, Anal. Chem. 1981, 53, 1492–1497.*
E. D. Hardin et al, Anal. Chem. 1984, 56, 2–7.*
T. P. Fan et al, Anal. Chem. 1984, 56, 1870–1876.*
G. M. Kresbach et al, J. Chromatog. 1987, 394, 89–100.*
E. R. Verheij et al, J. Chromatog. 1989, 474, 275–283.*
X. Fei et al, Anal. Chem. 1996, 68, 1143–1147.*
H. Zhang et al, J. Mass Spectrom. 1996, 31, 1039–1046.*
J. L. Dwyer ACS Symp. Ser. 1999, 731, 84–94.*

* cited by examiner

*Primary Examiner*—Arlen Soderquist
(74) *Attorney, Agent, or Firm*—Knobbe Martens Olson & Bear, LLP

(57) ABSTRACT

With rotating and translating a rotation-translation drum installed in a vacuum chamber of a mass spectrometry interface to constitute a mass spectro-meter, a liquid sample incorporating a dissolved substance to be analyzed in its mass is emitted for the drum from a sample supplying nozzle of the mass spectrometry interface, and the dissolved substance is isolated as a spiral filament on the drum. Then, a laser beam is irradiated onto the filament from a laser source via a laser beam inlet situated at the vacuum chamber and thereby, the dissolved substance is ionized without exposing to the air.

11 Claims, 1 Drawing Sheet

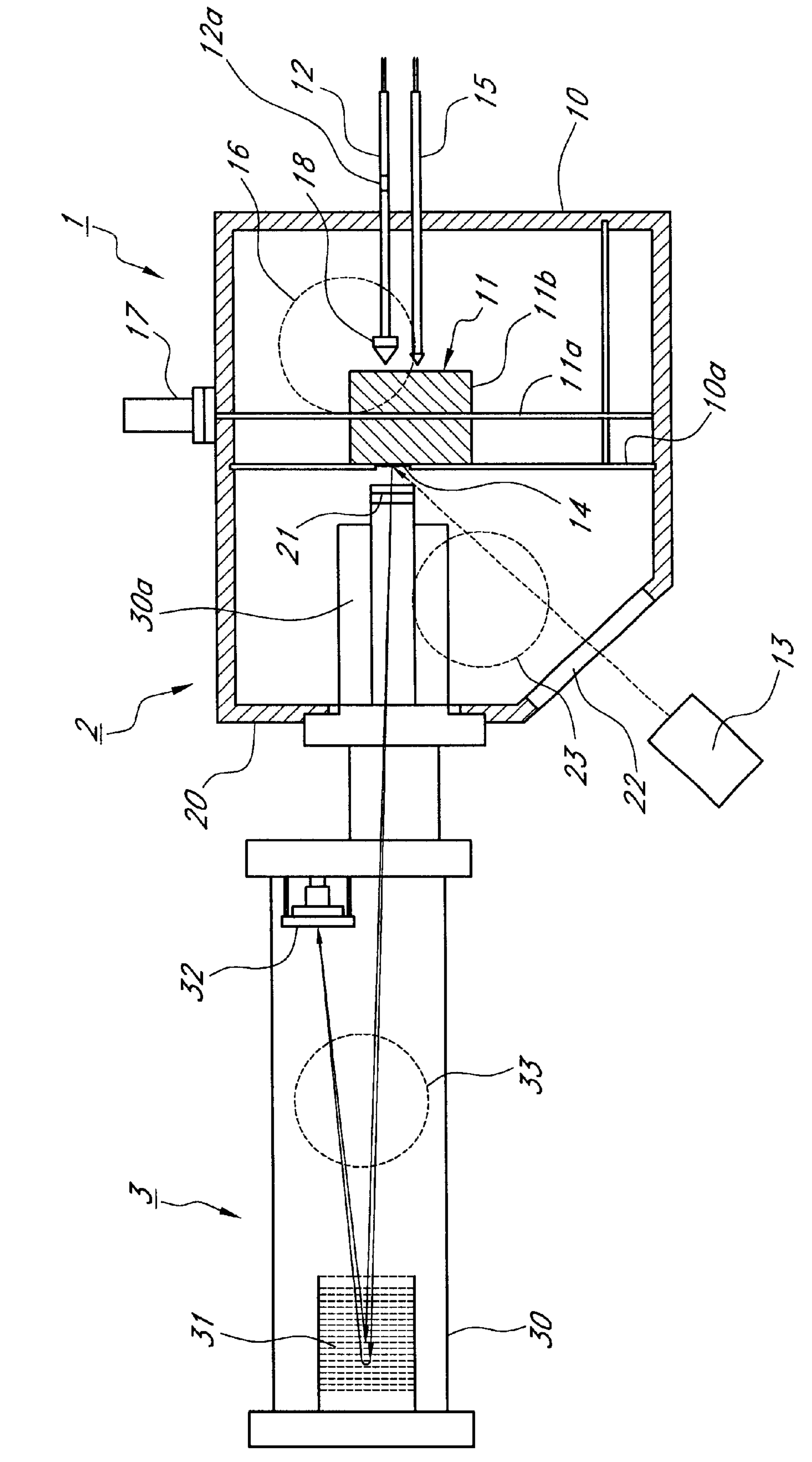
12a
12
15
10
16
18
11
11b
11a
10a
1
17
14
21
30a
13
2
20
23
22
32
33
3
31
30

MASS SPECTROMETRY INTERFACE, A MASS SPECTROMETER AND A MASS SPECTROMETRY

BACKGROUND OF THE INVENTION

1) Field of the Invention

This invention relates to a mass spectrometry interface, a mass spectrometer and a mass spectrometry, more particularly to a mass spectrometry interface, a mass spectrometer and a mass spectrometry preferably usable for a mass spectrometry of a liquid sample, a liquid chromatograph, or a biological sample and an ionization spectroscopic analysis 2) Description of the Prior Art Conventionally, a Matrix-Assisted Laser Deposition Ionization (MALDI) method or an electro spray method is employed for measuring a mass spectrum of a nonvolatile large mass molecule, and thus, the mass spectrum measuring technique is being widely applied for chemical fields or biological fields.

In the MALDI method, for enhancing the ionization of a dissolved substance to be analyzed in its mass, a large amount of matrix reagent is added into the sample solution incorporating the dissolved substance, and then, the thus obtained liquid sample is dropped onto a given plate to be evaporated and crystallized. Then, the plate is introduced into a mass spectrometer and irradiated by a laser beam to ionize the dissolved substance for its mass spectrometry.

In the electro spray method, a high voltage is applied to a nozzle to emit the liquid sample incorporating the dissolved substance, and thereby, the solvent of the liquid sample is desorbed and the dissolved substance is ionized. Then, the ionized dissolved substance is directly introduced into a mass spectrometer to be analyzed in its mass.

In the above electro splay method, an electrolyte is added to the liquid sample in order to enhance the ionization of the dissolved substance. Moreover, methanol, acetinitrile or the like to destroy the structure of a water is incorporated in the liquid sample for enhancing the desorption.

However, in the MALDI method, the liquid sample incorporating the dissolved substance may be often denaturalized due to much matrix reagent. Therefore, the MALDI method can not be applied for a liquid sample chemically changeable in short time and a long time-continuous measurement such as a mass spectrometry of a liquid chromatograph.

The electro spray method can not be also applied for the chemically changeable liquid sample and the long time-continuous measurement due to the denature of the liquid sample through the high voltage application. Moreover, if it is attempted that the denature of the liquid sample is prevented, the kind of the usable solvent is restricted. And then, if an associative solvent is employed in order to prevent the denature of the liquid sample, the clusters generated from the solvent molecules adheres to the solute species, and thus, the noises due to the clusters are superimposed on the mass spectrometry results of the dissolved substance.

SUMMERY OF THE INVENTION

It is an object of the present invention to provide a new mass spectrometer and mass spectrometry without the above matters.

For achieving the above object, the first invention relates to a mass spectrometry interface to constitute a mass spectrometer which comprises a vacuum chamber with a laser beam inlet, a metallic rotation-translation drum installed in the vacuum chamber, a sample supplying nozzle to emit and stabilize a liquid sample incorporating a dissolved substance to be analyzed in its mass for and onto the rotation-translation drum, and a laser source to irradiate a laser beam onto the dissolved substance from the laser beam inlet and to ionize the dissolved substance.

The second invention relates to a mass spectrometer to directly achieve the above object which comprises the above mass spectrometry interface or the following preferred mass spectrometry interface, an ion accelerating electrode part, and an mass spectrometry part.

Moreover, the third invention relates to a mass spectrometry using the above mass spectrometry interface or the mass spectrometer, comprising the steps of:

evacuating up to a given vacuum degree the interior of a vacuum chamber of a mass spectrometry interface constituting a mass spectrometer, emitting a liquid sample incorporating a dissolved substance to be analyzed in its mass for a rotation-translation drum from a sample supplying nozzle of the mass spectrometry interface and thereby, stabilizing the dissolved substance on the rotation-translation drum, and irradiating a laser beam for the stabilized dissolved substance from a laser source of the mass spectrometry interface via a laser beam inlet formed at the vacuum chamber and thereby, ionizing the dissolved substance.

According to the first through third inventions, only the dissolved substance to be analyzed in its mass is isolated on the metallic rotation-translation drum installed in the vacuum chamber, and a laser beam is directly irradiated on the deposited substance. Therefore, the substance isolated on the metal surface is ionized at high efficiency, and thus, an extreme high sensitive and efficient mass spectrometry can be performed.

The dissolved substance can fixed continuously as a long spiral belt on the rotation-translation drum. Therefore, the mass spectrometer and mass spectrometry of the present invention can be preferably employed for a long time-continuous measurement such as a mass spectrometry of a liquid chromatograph.

Therefore, much matrix reagent is not required, different from the MALDI method, and a high voltage is not also required, different from the electro-spray method. As a result, the denature of the liquid sample can be prevented, and the noises due to the clusters can be also prevented.

BRIEF DESCRIPTION OF THE DRAWINGS

For better understanding of the present invention, reference is made to the attached drawings, wherein FIGURE is a schematic view showing an embodiment of the mass spectrometry of the present invention.

DESCRIPTION OF THE PREFERRED EMBODIMENTS

FIGURE is a structural view schematically showing an embodiment of the mass spectrometry of the present invention.

The depicted mass spectrometry has a mass spectrometry interface 1, an ion accelerating electrode part 2 and a mass spectrometry part 3, according to the present invention.

The mass spectrometry part 1, according to the present invention, has a vacuum chamber 10 with a laser beam inlet 14, a rotation-translation drum 11 provided in the vacuum chamber 10, a sample supplying nozzle 12 to emit a liquid sample incorporating a dissolved substance to be analyzed in its mass for the rotation-translation drum 11, and a laser source 13 to ionize the dissolved substance deposited on the rotation-translation drum 11.

Moreover, a nozzle 15 to enhance the ionization of the dissolved substance through the formation of an optical absorption layer made of an optical absorption material on the rotation-translation drum is provided. The nozzle 15 is not essential in the present invention, but it can develop the detection sensitivity of the mass spectrometry of the present invention.

The rotation-translation drum 11 has a double structure of a shaft 11A and a thin titanium tube 11B supported by spokes. A driving unit 17 to rotate and translate the rotation-translation drum 11 is provided on the outer surface of the upper chamber wall of the vacuum chamber 10, and transmits its rotation and translation driving force to the drum 11 through the shaft 11A.

The rotation-translation drum 11 may have another construction, but the above double structure is simple, so the drum 11 can be made to be light in its weight and the rotation and translation movement can be easily operated.

A cryopump 16 is positioned at the area denoted by a broken line in the vacuum chamber 10, and thus, the solvent such as a water of the liquid sample is evacuated efficiently and the interior of the vacuum chamber 10 can be maintained at a relatively high vacuum degree.

Moreover, since a heating cap 18 is provided at the forefront of the sample supplying nozzle 12, the condensation of the liquid sample due to the rapid temperature drop through its adiabatic expansion can be prevented when the liquid sample is emitted for the rotation-translation drum 11 in the vacuum chamber 10. In a preferred embodiment, the liquid sample is maintained constantly at a temperature of not lower than 27° C. (300K).

Furthermore, since a filter 12A is provided in the sample supplying nozzle 12, only the dissolved substance particles having a given size or smaller are passed through the nozzle 12 and emitted for the rotation-translation drum 11. Thereby, the stuffiness of the sample supplying nozzle 12 is prevented, and the dissolved substance is fixed onto the metal surface of the rotation-translation drum 11 idealistically. As a result, the ionization efficiency can be developed extremely.

In a preferred embodiment of the present invention, the filter passes only the dissolved substance particles having sizes of not more than 10 $\mu$m.

The sample supplying nozzle 12 may be composed of a stainless steel pipe or a titanium pipe having a 1/16 inch outer diameter and a 250 $\mu$m or below inside diameter.

The ion accelerating electrode part 2 has a first high vacuum chamber 20 and an accelerating electrode 21. In FIGURE, the vacuum chamber 10 constituting the mass spectrometry interface 1 and the first high vacuum chamber 20 are united via the chamber wall 10A of the vacuum chamber 20.

Because of the unification of the above vacuum chamber, the ion accelerating electrode chamber part 2 has a laser beam- introducing window 22 to introduce a laser beam from the laser source 13 onto the rotation-translation drum 11 via the laser beam inlet 14. Moreover, since a vacuum pump 23 such as a cryopump is positioned at the area denoted by a broken line in the first high vacuum chamber 20, the interior of the chamber 20 is evacuated up to high vacuum degree.

In FIGURE, the laser beam inlet 14 is formed at the opposite side position of the chamber wall 10A of the vacuum chamber 10 to the sample supplying nozzle 12 for the rotation-translation drum 11. Thereby, the contamination in the ion accelerating electrode part 2, adjacent to the laser beam inlet 14, due to the liquid sample emitted from the sample supplying nozzle 12 can be prevented efficiently. Moreover, the ionized dissolved substance can be taken out efficiently, and thus, the mass spectrometry sensitivity can be enhanced.

Only if the above effects are attained, the laser beam inlet 14 may be formed at the upper side or the lower side of the chamber wall 10A. However, if the laser beam inlet is situated at the above position, the prevention of the contamination and the enhancement of the mass spectrometry sensitivity can be performed at the most.

The mass spectrometry part 3 has a second high vacuum chamber 30, a reflectron-reflective electrode 31 and a detector 32. In the mass spectrometer depicted in FIGURE, the forefront tube 30A of the second high vacuum chamber 30 is directly inserted into the first high vacuum chamber 20, and thereby, the ionized dissolved substance which is accelerated at the accelerating electrode 21 is taken out efficiently.

The reflectron-reflective electrode 31 and the detector 32 are commercially available.

Moreover, a vacuum pump 33 such as a cryo pump is positioned at the area denoted by a broken line in the second high vacuum chamber 30 to evacuate the interior of the chamber.

Next, a mass spectrometry using the above mass spectrometer shown in FIGURE.

First, the interior of the vacuum chamber 10 in the mass spectrometry interface 1 is evacuated up to a given vacuum degree. Subsequently, the liquid sample is emitted for the rotation-translation drum 11 from the sample supplying nozzle 12 with rotating and translating the drum 11. Just then, the liquid sample exhibits phase-transition to a mixture of gas and solid, and only the thus obtained dissolved substance of the liquid sample is stabilized as a solid spiral line on the drum 11.

Then, a laser beam is irradiated onto the isolated substance from the laser source 13 via the laser beam introducing window 22 and the laser beam inlet 14. In this time, the isolated substance is ionized and introduced into the ion accelerating electrode part 2 from the laser beam inlet 14. Thereafter, the ionized substance is accelerated by the accelerating electrode 21, and introduced into the mass spectrometry part 3 through the forefront tube 30A of the second vacuum chamber 30.

The ionized dissolved substance, which is accelerated as mentioned above, approaches to the reflectron-reflective electrode 31 and compensated in its kinetic energy fluctuation, and then, reaches the detector 32.

The above operation is carried out continuously with rotating and translating the rotation-translating drum 11. That is, the continuous irradiation of the laser beam enables the isolated substance to be detected continuously at high ionization, so that the detection sensitivity of the mass spectrometry can be enhanced. Moreover, since in this mass spectrometry, a sample which is apt to be chemically denaturalized is not employed and such a high detection sensitivity is attained, the mass spectrometry can be performed precisely.

Therefore, the above long time-continuous mass spectrometry for a liquid chromatograph, etc. can be carried out precisely.

Moreover, due to the small ionization efficiency of the isolated substance, the substance may not sometimes ionized effectively only by the laser beam irradiation, and thus, the detection sensitivity may not be enhanced effectively. In this case, the ionization of the light harvesting substance is developed by the ionization enhancing nozzle 15, and thereafter, the solute substance on the layer of light harvesting substance is secondary ionized and analyzed in its mass.

Concretely, before the liquid sample is emitted from the sample supplying nozzle 12, an optical absorption material is emitted for the rotation-translation drum 11 from the ionization enhancing nozzle 15 with rotating and translating the drum 11, and then, an optical absorption layer made of the optical absorption material is formed on the drum 11.

Subsequently, as mentioned above, the liquid sample is emitted for the rotation-translation drum 11 from the sample supplying nozzle 12. In this case, the solute substance of the liquid sample is located at the surface area of the optical absorption layer. And, when the laser beam is irradiated onto the located solute substance, the ionization of the solute substance is developed indirectly through the location effect of the solute substance and the optical absorption effect of the optical absorption layer. As a result, the detection sensitivity of the mass spectrometry is developed from the increase of the ionization of the solute substance, and thus, the above advantages are attained.

Although the present invention was described in detail with reference to the above examples, this invention is not limited to the above disclosure and every kind of variation and modification may be made without departing from the scope of the present invention.

As mentioned above, according to the present invention, the ionization of the dissolved substance can be enhanced only by the laser beam irradiation without the addition of the above matrix reagent or the application of the high voltage. Therefore, the detection sensitivity of the mass spectrometer can be developed and thus, the long time-continuous mass spectrometry can be performed precisely.

What is claimed is:

1. A mass spectrometry interface comprising a vacuum chamber with a laser beam inlet, a rotation-translation drum installed in the vacuum chamber, said rotation-translation drum having a metallic surface and being capable of rotating and translating the surface of the drum, a sample supplying nozzle to emit and stabilize a liquid sample incorporating solute substance to be isolated and analyzed in its mass for and onto the metallic surface of the rotation-translation drum, and a laser source to irradiate a laser beam onto the dissolved substance from the laser beam inlet and to ionize the isolated substance.

2. A mass spectrometry interface as defined in claim 1, wherein the laser beam inlet is situated at the opposite position of the vacuum chamber to the sample supplying nozzle with the rotation-translation drum in therebetween.

3. A mass spectrometry interface as defined in claim 1, wherein the rotation-translation drum has a double structure composed of a shaft and a cylindrical titanium rim connected to the shaft.

4. A mass spectrometry interface as defined in claim 1, wherein the sample supplying nozzle has a heating cap at its forefront.

5. A mass spectrometry interface as defined in claim 1, wherein the sample supplying nozzle has a filter therein.

6. A mass spectrometry interface as defined in claim 1, further comprising a nozzle to enhance the ionization of the solute substance through the preliminary emission of an optical absorption material for the rotation-translation drum and thus the formation of an optical absorption layer made of the optical absorption material between the metal and the sample layers.

7. A mass spectrometer comprising a mass spectrometer interface as defined in claim 1, an ion accelerating electrode part and a mass spectrometry part.

8. A mass spectrometer as defined in claim 7, wherein the ion accelerating electrode part comprises a first high vacuum chamber and an accelerating electrode.

9. A mass spectrometer as defined in claim 7, wherein the mass spectrometry part comprises a second high vacuum chamber, a reflectron-reflective electrode and a detector.

10. A mass spectrometry method comprising the steps of:

evacuating up to a given vacuum degree the interior of a vacuum chamber of a mass spectrometry interface constituting a mass spectrometer, emitting a liquid sample incorporating a dissolved substance to be analyzed in its mass to a rotation-translation drum from a sample supplying nozzle of the mass spectrometry interface and thereby, isolating the dissolved substance on the rotation-translation drum by rotating and translating the drum, and irradiating the isolated solute substance with a laser beam from a laser source of the mass spectrometry interface via a laser beam inlet formed at the vacuum chamber and thereby, ionizing the solute substance.

11. A mass spectrometry as defined in claim 10, further comprising the step of emitting an optical absorption material for the rotation-translation drum from a nozzle to enhance the ionization of the dissolved substance and then, forming an optical absorption layer made of the optical absorption material thereon with rotating and translating the rotation-translation drum before the liquid sample is emitted for the rotation-translation drum and the dissolved substance of the liquid sample is isolated thereon.

* * * * *